United States Patent
Lincoln et al.

(10) Patent No.: US 6,665,564 B2
(45) Date of Patent: Dec. 16, 2003

(54) CARDIAC RHYTHM MANAGEMENT SYSTEM SELECTING A-V DELAY BASED ON INTERVAL BETWEEN ATRIAL DEPOLARIZATION AND MITRAL VALVE CLOSURE

(75) Inventors: William C. Lincoln, Coon Rapids, MN (US); Gerrard M. Carlson, Champlin, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 09/862,763

(22) Filed: May 21, 2001

(65) Prior Publication Data

US 2002/0173826 A1 Nov. 21, 2002

(51) Int. Cl.$^7$ ............................................. A61N 1/365
(52) U.S. Cl. ............................................. 607/17; 607/9
(58) Field of Search ............................... 607/9, 17, 18

(56) References Cited

U.S. PATENT DOCUMENTS

| | | | |
|---|---|---|---|
| 5,540,727 A | 7/1996 | Tockman et al. | 607/18 |
| 5,674,256 A | 10/1997 | Carlson | 607/17 |
| 5,700,283 A | 12/1997 | Salo | 607/17 |
| 5,836,987 A * | 11/1998 | Baumann et al. | 607/17 |
| 6,070,100 A * | 5/2000 | Bakels et al. | 607/9 |
| 6,223,082 B1 | 4/2001 | Bakels et al. | 607/17 |

OTHER PUBLICATIONS

Cazeau, S., et al., "Multisite stimulation of correction of cardiac asynchrony", *Heart*, 84, pp. 579–581, (2000).

Kostis, J.B., "Mechanisms of heart sounds", *American Heart Journal*, 89 (4), Letter to the Editor, p. 546–547, (Apr. 1975).

Leonelli, F.M., et al., "Systolic and Diastolic Effects of Variable Atrioventricular Delay in Patients With Complete Heart Block and Normal Ventricular Function", *The American Journal of Cardiology*, 80, pp. 294–298, (Aug. 1997).

Ritter, P., et al., "Determination of the optimal atrioventricular delay in DDD pacing", *Europace*, 1, pp. 126–130, (1999).

Ritter, P., et al., "New Method for Determining the Optimal Atrio–Ventricular Delay in Patients Paces in DDD Mode for Complete Atrio–Ventricular Block", *Pace*, 18, Abstact No. 237, p. 855, (Apr. 1995).

Waider, W., et al., "First Heart Sound and Ejection Sounds: Echocardiographic and Phonocardiographic Correlation with Valvular Events", *The American Journal of Cardiology*, 35, pp. 346–356, (Mar. 1975).

* cited by examiner

*Primary Examiner*—George R. Evanisko
*Assistant Examiner*—Omar Khan
(74) *Attorney, Agent, or Firm*—Schwegman, Lundberg, Woessner & Kluth, P.A.

(57) ABSTRACT

A cardiac rhythm management system selects an atrioventricular (A-V) delay based on a time-interval between an atrial depolarization and mitral valve closure (MVC). For several different A-V delays, the system measures time intervals between atrial depolarizations (i.e., sensed or paced P-waves) and accelerometer-detected MVCs. Based on this information, the system selects a particular A-V delay for improving cardiac output during subsequent delivery of cardiac rhythm management therapy.

12 Claims, 5 Drawing Sheets

CARDIAC RHYTHM MANAGEMENT SYSTEM SELECTING A-V DELAY BASED ON INTERVAL BETWEEN ATRIAL DEPOLARIZATION AND MITRAL VALVE CLOSURE

TECHNICAL FIELD

The present system relates generally to cardiac rhythm management systems and particularly, but not by way of limitation, to such a system selecting A-V delay based on interval between an atrial depolarization and a mitral valve closure.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Some pacers coordinate atrial and ventricular contractions to improve pumping efficiency. Cardiac rhythm management systems also include coordination devices for coordinating the contractions of both the right and left sides of the heart for improved pumping efficiency.

Cardiac rhythm management systems also include defibrillators that are capable of delivering higher energy electrical stimuli to the heart. Such defibrillators also include cardioverters, which synchronize the delivery of such stimuli to sensed intrinsic heart depolarizations. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the proper timing relationship between a sensed or paced atrial depolarization and the subsequent delivery during the same cardiac cycle of a ventricular pacing pulse. This atrioventricular time interval is referred to as the A-V delay. The A-V delay provided by a cardiac rhythm management system may be programmed by the physician to tailor the therapy for a particular patient. The actual value of the A-V delay affects the blood flow from the atrium to the ventricle and, therefore, affects the cardiac output of the heart. The blood flow from the atrium to the ventricle has two components. After the ventricle has completed a contraction, it begins to relax, with blood entering the ventricle from the corresponding atrium when the atrial pressure exceeds the ventricular pressure. This pulse-like fluid flow is sometimes referred to as the "E-wave" of a Doppler echocardiograph. Next, the atrium contracts to actively expel a second pulse-like flow of fluid, sometimes referred to as the Doppler echocardiographic "A-wave," to the ventricle. For a given fixed time interval between ventricular contractions, if the A-V delay is set too long, then the atrial contraction is moved closer to the preceding ventricular contraction. Because the A-wave and the E-wave occur closer together in time, there is a reduction in total ventricular filling time. By contrast, if the A-V delay is set too short, then the ventricle does not receive the full benefit of the blood flow during the A-wave. For these and other reasons, there is a need to select an A-V delay value that promotes increased blood flow from the atrium to the ventricle, thereby increasing cardiac output.

SUMMARY

This document discusses a cardiac rhythm management system that, among other things, selects an A-V delay based on an interval between an atrial depolarization and a mitral valve closure.

In one embodiment, the system includes a method in which ventricular stimulations are provided. The ventricular stimulations are separated from corresponding preceding atrial depolarizations, occurring during the same cardiac cycle, by different atrioventricular (A-V) delays. The system detects mitral valve closures associated with each pair of atrial and ventricular stimulations. The system measures P-MVC time intervals between the atrial depolarizations and the mitral valve closures. In one embodiment, the slopes of the P-MVC time intervals are calculated against the different A-V delays. Based on the slopes, an A-V delay is selected for subsequent delivery of ventricular stimulations. In an alternate embodiment, linear approximations of the P-MVC time intervals (as a function of the different A-V delays) are used for selecting the A-V delay.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
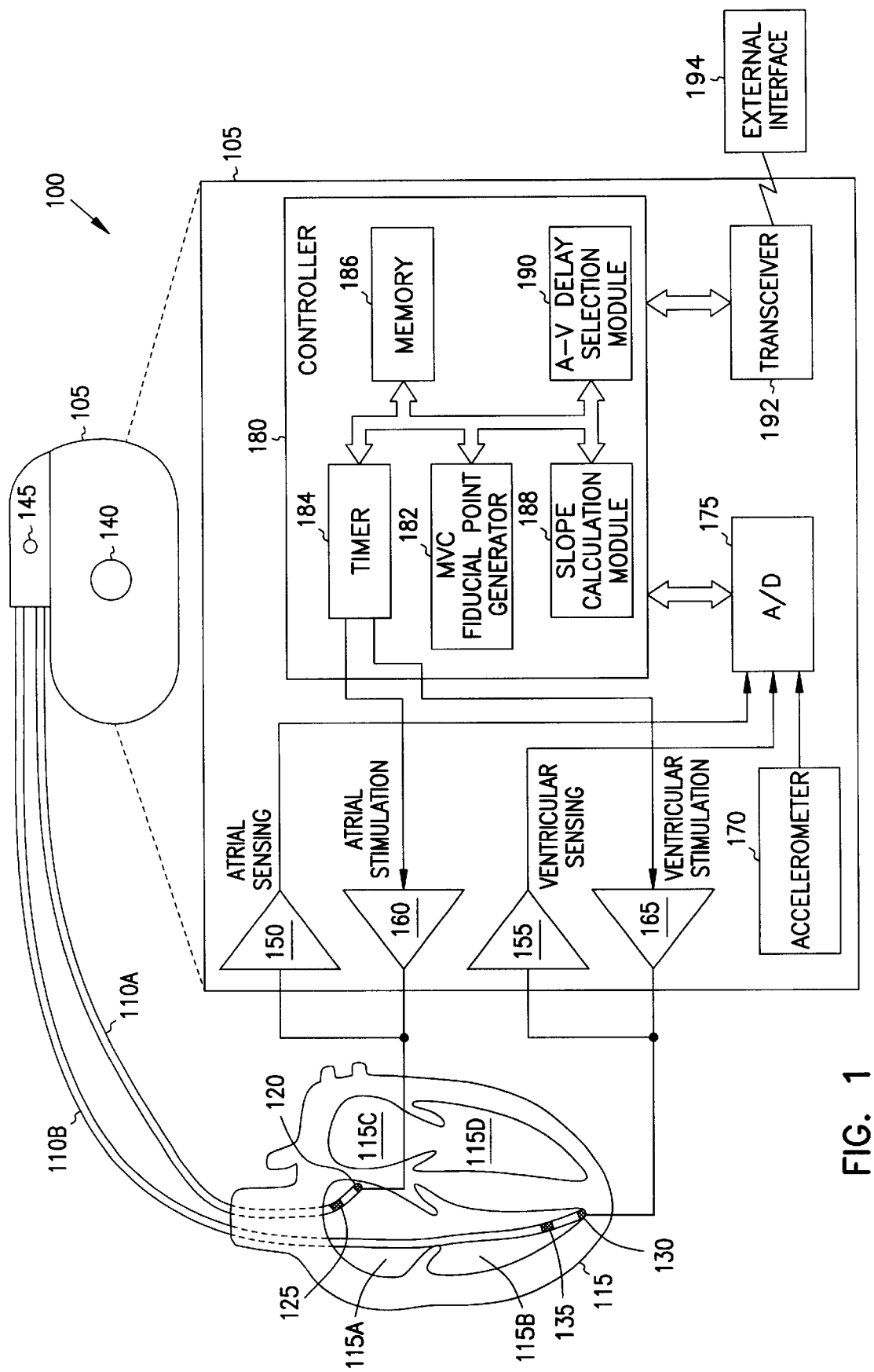
FIG. 1 is a schematic/block diagram illustrating generally, among other things, one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. The term "and/or" refers to a nonexclusive "or" (i.e., "A and/or B" includes both "A and B" as well as "A or B").

This document discusses a cardiac rhythm management system that, among other things, selects an A-V delay based on an interval between an atrial depolarization and a mitral valve closure. The present methods and apparatus will be described in applications involving implantable medical devices including, but not limited to, implantable cardiac rhythm management systems such as pacemakers, cardioverter/defibrillators, pacer/defibrillators, biventricular or other multi-site coordination devices, and drug delivery systems. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders, whether such devices are used for providing a diagnostic, a therapy, or both a diagnostic and a therapy.

FIG. 1 is a schematic/block diagram illustrating generally one embodiment of portions of the present cardiac rhythm management system 100 and an environment in which it is used. In this embodiment, system 100 includes, among other things, cardiac rhythm management device 105, which is coupled by leads 110A–B to heart 115. Heart 115 includes four chambers: right atrium 115A, right ventricle 115B, left atrium 115C, and left ventricle 115D.

In one embodiment, lead 110A includes an electrode associated with right atrium 115A, such as tip electrode 120 and/or ring electrode 125. The electrode is "associated" with the particular heart chamber by inserting it into that heart chamber, or by inserting it into a portion of the heart's vasculature that is close to that heart chamber, or by epicardially placing the electrode outside that heart chamber, or by any other technique of configuring and situating an electrode for sensing signals and/or providing therapy with respect to that heart chamber. Lead 110B, which in one embodiment is introduced into right ventricle 115B, includes an electrode associated with right ventricle 115B, such as electrodes 130 and 135. Device 105 may also include other electrodes, such as housing electrode 140 and/or header electrode 145, which are also associated with heart 115, and which are useful for, among other things, "unipolar" sensing of heart signals or unipolar delivery of contraction-evoking stimulations in conjunction with one or more of the electrodes 120, 125, 130, and 135 associated with heart 115. Alternatively, "bipolar" sensing and/or therapy may be used between electrodes 120 and 125, and between each of electrodes 130 and 135 and another closely situated electrode (not shown).

In one embodiment, device 105 includes an atrial sensing module 150 and a ventricular sensing module 155, which are each coupled to one or more of the electrodes, such as electrodes 120 and 130, respectively, for sensing intrinsic and/or evoked electrical depolarizations corresponding to heart chamber contractions. Such electrical depolarizations of the heart tissue include atrial depolarizations, referred to as P-waves, and ventricular depolarizations, referred to as QRS complexes. The QRS complex is a rapid sequence of three signal excursions away from a baseline in sequentially switching polarity, with the first excursion referred to as a Q-wave, the second (typically the largest) excursion referred to as an R-wave, and the third excursion referred to as the S-wave. Device 105 also includes atrial stimulation module 160 and ventricular stimulation module 165, respectively coupled, in this example, to atrial electrode 120 and ventricular electrode 130 for providing stimulation energy pulses thereto. Such stimulation energy pulses typically evoke heart contractions of the heart chambers with which their respective electrodes are associated.

Device 105 also includes a mitral valve closure detector that, in one embodiment, includes accelerometer 170. In one embodiment, accelerometer 170 is carried within the housing of device 105, which is pectorally or abdominally implanted in close enough proximity to heart 115 to sense acceleration from heart 115. Accelerometer 170 outputs a heart acceleration signal to analog-to-digital (A/D) converter 175, for conversion into a digitized signal along with the atrial heart signal output by atrial sensing module 150 and the ventricular heart signal output by ventricular sensing module 155. A/D converter is coupled to controller 180 for providing these digital signals to controller 180.

Controller 180 includes hardware components and/or microcontroller or microcontroller-like executable operations that implement an accelerometer interface such as mitral valve closure (MVC) fiducial point generator 182, a timer 184, a memory 186, a slope calculation module 188, and an atrioventricular (A-V) delay selection module 190. MVC fiducial point generator 182 is coupled to accelerometer 170 through A/D converter 175 such that it receives a digitized heart acceleration signal. Based upon this digitized heart acceleration signal, MVC fiducial point generator 182 detects mitral valve closures of heart 115 and provides MVC fiducial points associated with the occurrence of such mitral valve closures.

Timer 184 is coupled to atrial stimulation circuit 160 and/or ventricular stimulation circuit 165 for delivering timing signals that control the delivery of the atrial and/or ventricular stimulation pulses. In an embodiment employing atrial sensing and/or pacing as well as ventricular pacing and/or sensing, these timing signals determine the A-V delay time interval between successive atrial and ventricular senses/stimulations occurring during the same cardiac cycle. Timer 184 also measures the time interval, referred to as a P-MVC time interval, between an atrial contraction (measured either from the issuance of an atrial stimulation pulse or, alternatively, from the detection of a sensed intrinsic or evoked atrial contraction) and a next MVC fiducial point detected by accelerometer 170.

Timer 184 measures the P-MVC time intervals over several cardiac cycles for which the A-V delay between delivered or sensed atrial and ventricular contractions is varied over a range of values such as, by way of example, but not by way of limitation, approximately between 10 milliseconds and 250 milliseconds, inclusive, at increments that are approximately between 10 milliseconds and 50 milliseconds, inclusive. The measured P-MVC time intervals and corresponding A-V delay values are stored in memory locations in memory 186. Based on this data, slope calculation module 188 calculates the slope of the P-MVC time intervals against corresponding adjacent A-V delay values, by taking a difference between adjacent P-MVC time intervals divided by a difference between corresponding adjacent A-V delay values. The resulting calculated slopes are stored in memory locations in memory 186. Based on these calculated slopes, A-V delay selection module 190 determines an appropriate A-V delay for use in subsequent delivery of ventricular stimulations to heart 115 in conjunction with either intrinsic or paced atrial heart depolarizations. In a further embodiment, an indication of the appropriate A-V delay as determined by A-V delay selection module 190 is provided to transceiver 192, which is coupled to controller 180, and transmitted to external interface 194 for display to a physician or other user, such as on a computer monitor, printout, or other data output mechanism.

Figure 2:
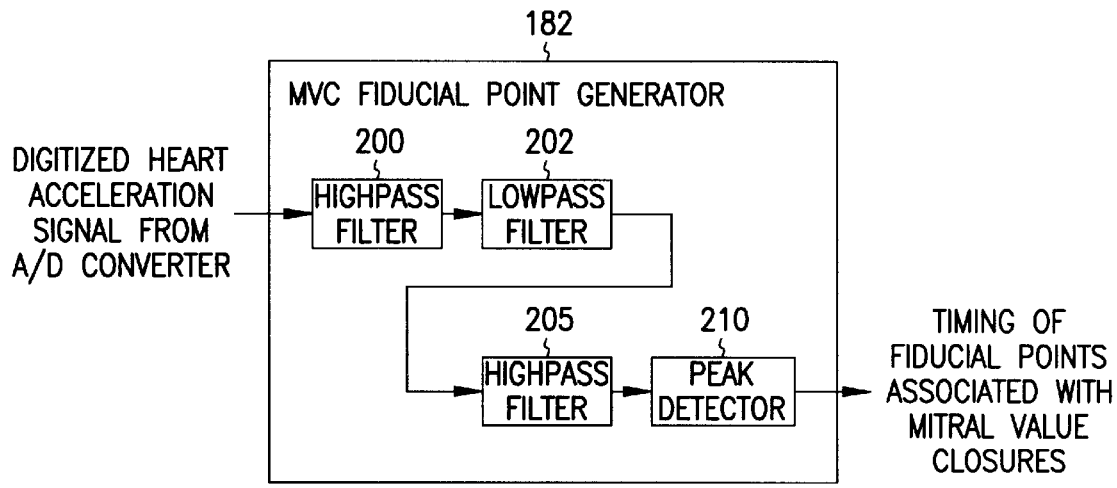
FIG. 2 is a schematic/block diagram illustrating generally one embodiment of portions of a mitral valve closure fiducial point generator.

FIG. 2 is a schematic/block diagram illustrating generally one embodiment of portions of MVC fiducial point generator 182, including a highpass filter 200, a lowpass filter 202, a highpass filter 205, and a peak detector 210, although it is understood that certain of these components could be combined rather than implemented separately (e.g., a highpass and lowpass filter could be combined into a bandpass filter, etc.). In one embodiment, highpass filter 200 receives the digitized heart acceleration signal from A/D converter 175, removes baseline (i.e., constant or low frequency drift) signal components, and provides a resulting output signal to an input of lowpass filter 202. In this example, lowpass filter 202 is a 5-sample moving average "boxcar" filter attenuating signal frequencies above approximately 100 Hz. Lowpass filter 202 receives the baseline-filtered heart acceleration signal from highpass filter 200, and outputs a resulting lowpass filtered heart acceleration signal to an input of highpass filter 205. In one embodiment, highpass filter 205 is a differentiator that takes a first derivative of its input lowpass filtered heart acceleration signal received from the output of lowpass filter 202 and outputs a resulting first derivative heart acceleration signal to an input of peak detector 210. In one embodiment, peak detector 210 detects negative peaks of the first derivative heart acceleration signal. However, it is understood that a polarity reversal of accelerometer 170 and/or signal inversion(s) in the signal processing path of the heart acceleration signal may alternatively require a detection of positive peaks of the first derivative heart acceleration signal. For each cardiac cycle, the first negative peak of the first derivative heart acceleration signal occurring after the delivery of a ventricular stimulation and before the next intrinsic or paced atrial depolarization is deemed an MVC fiducial point associated with the mitral valve closure. An indication of the time at which such MVC fiducial points occur is provided by MVC fiducial point generator 182 to timer 184 for calculation of the corresponding P-MVC time intervals discussed above.

Figure 3:
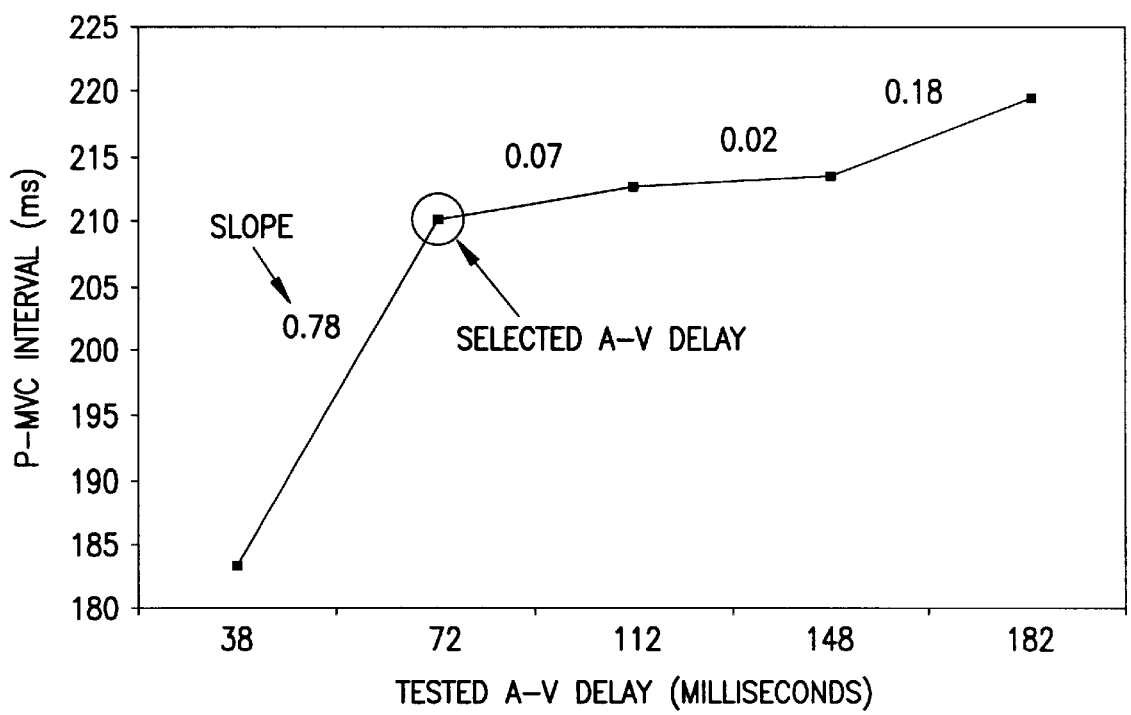
FIG. 3 is a graph illustrating an example of different P-MVC time intervals, between atrial depolarizations and corresponding subsequent mitral valve closures, obtained in response to different test A-V delays.

FIG. 3 is a graph illustrating an example of the different P-MVC time intervals obtained by timer 184 in response to five different A-V delays that were tested, with line segments drawn between the data points. In one embodiment of operation, slope calculation module 188 determines the slopes associated with each P-MVC line segment between corresponding adjacent tested A-V delay values, and stores an indication of such slopes in memory 186. Based on these slopes, A-V delay selection module 190 selects an A-V delay that is deemed appropriate for use in subsequent delivery of ventricular stimulations in conjunction with intrinsic or paced atrial depolarizations. In a very general sense, the shorter pairs of A-V delays typically manifest larger associated slopes than the longer pairs of A-V delays, at least when the extremes of the graph of FIG. 3 are inspected. In one embodiment, the appropriate A-V delay is selected by beginning at the shortest pair of adjacent A-V delay values, and working toward the longest pair of adjacent A-V delay values. The appropriate A-V delay is selected as the shortest of the A-V delay pairs with which an adjacent shorter one of the A-V delay pairs provides a larger slope than an adjacent longer one of the A-V delay pairs. This is illustrated in FIG. 3 by the selection of the second shortest A-V delay as the appropriate A-V delay for the timing of subsequent atrial and ventricular senses and/or stimulations, because, proceeding from shorter A-V delays to longer A-V delays, the second line segment manifests a smaller slope than the adjacent first line segment.

In another embodiment, the "knee" in the hockey stick shaped curve of FIG. 3 is obtained by extrapolating a line based on the shortest A-V delays, and a second line based on the longest A-V delays, determining the intersection of these two lines, and determining the associated A-V delay corresponding to the intersection. This technique, which does not require slope calculations, is illustrated generally by FIG. 4.

Figure 4:
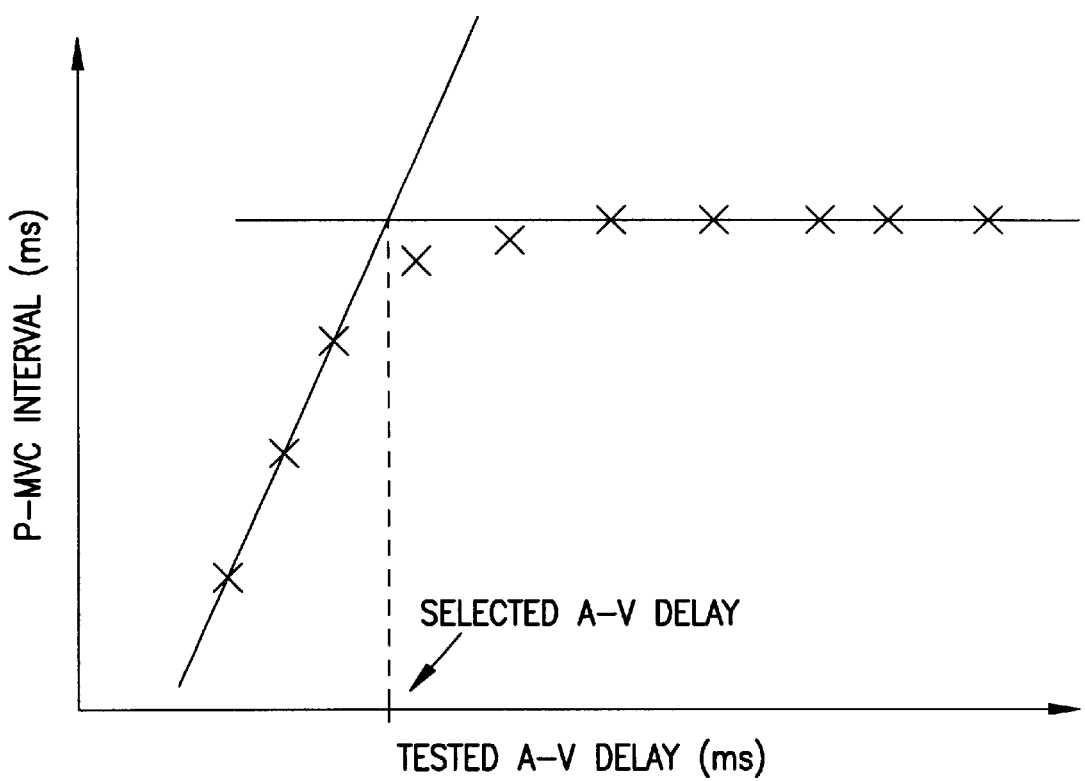
FIG. 4 is a graph illustrating generally a technique for selecting an A-V delay based on an intersection between a first linear approximation of P-MVC time intervals at short A-V delays and a second linear approximation of P-MVC time intervals at longer A-V delays.
Figure 5:
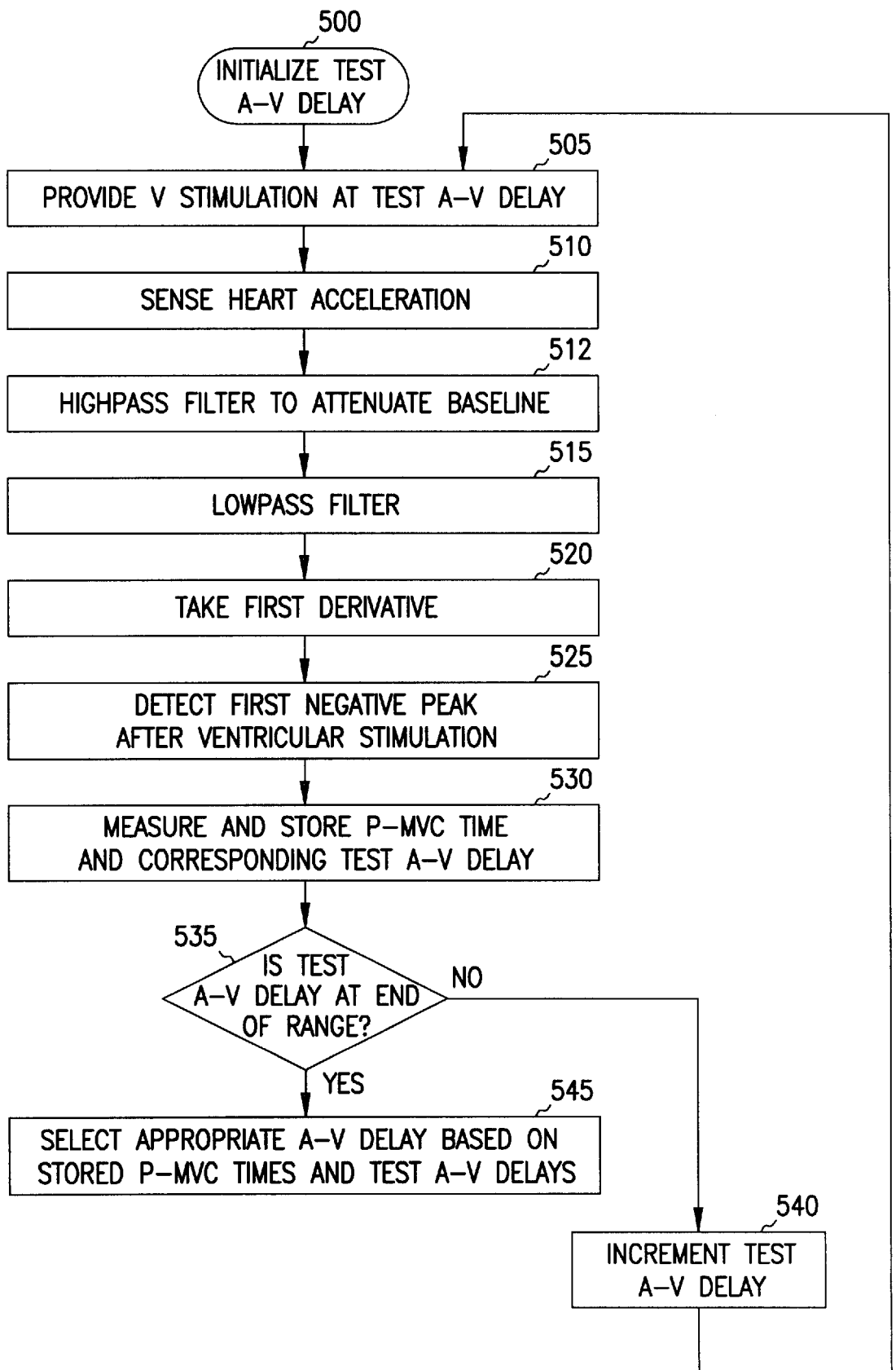
FIG. 5 is a flow chart illustrating generally one embodiment of an example technique for selecting an appropriate A-V delay at which to deliver subsequent ventricular stimulation therapy.

FIG. 5 is a flow chart illustrating generally one embodiment of an example technique for selecting an appropriate A-V delay at which to deliver subsequent ventricular stimulation therapy. At step 500, an test A-V delay is initialized, such as for example, to the lowest A-V delay value in a range of test A-V delay values. At step 505, a ventricular stimulation is delivered after an intrinsic or paced atrial depolarization, separated therefrom by a time equal to the test A-V delay. At step 510, a heart acceleration is sensed. At step 512, the baseline dc or low frequency component of the detected heart acceleration signal is removed by highpass filtering. At step 515, the heart acceleration signal is lowpass filtered. At step 520, the lowpass filtered heart acceleration signal is differentiated to obtain a resulting first derivative heart acceleration signal. At step 525, a first peak of the first derivative heart acceleration signal (i.e., in this case, a first negative peak occurring after the ventricular stimulation and before a next sensed or paced atrial depolarization) is detected and deemed a fiducial point associated with mitral valve closure for that cardiac cycle. At step 530, a P-MVC time interval is measured between the paced or intrinsic atrial depolarization and the corresponding subsequent MVC fiducial point during the same cardiac cycle. At step 535, if the test AV delay is not at the end of the range of test A-V delay values, the test A-V delay is incremented at step 540 and steps 505 through 535 are repeated. If, however, at step 535, the test A-V delay is at the end of the range of test A-V delay values, then at step 545 an appropriate A-V delay for subsequent delivery of ventricular stimulations is selected, such as by using the techniques described with respect to FIG. 3 or 4.

Figure 6:
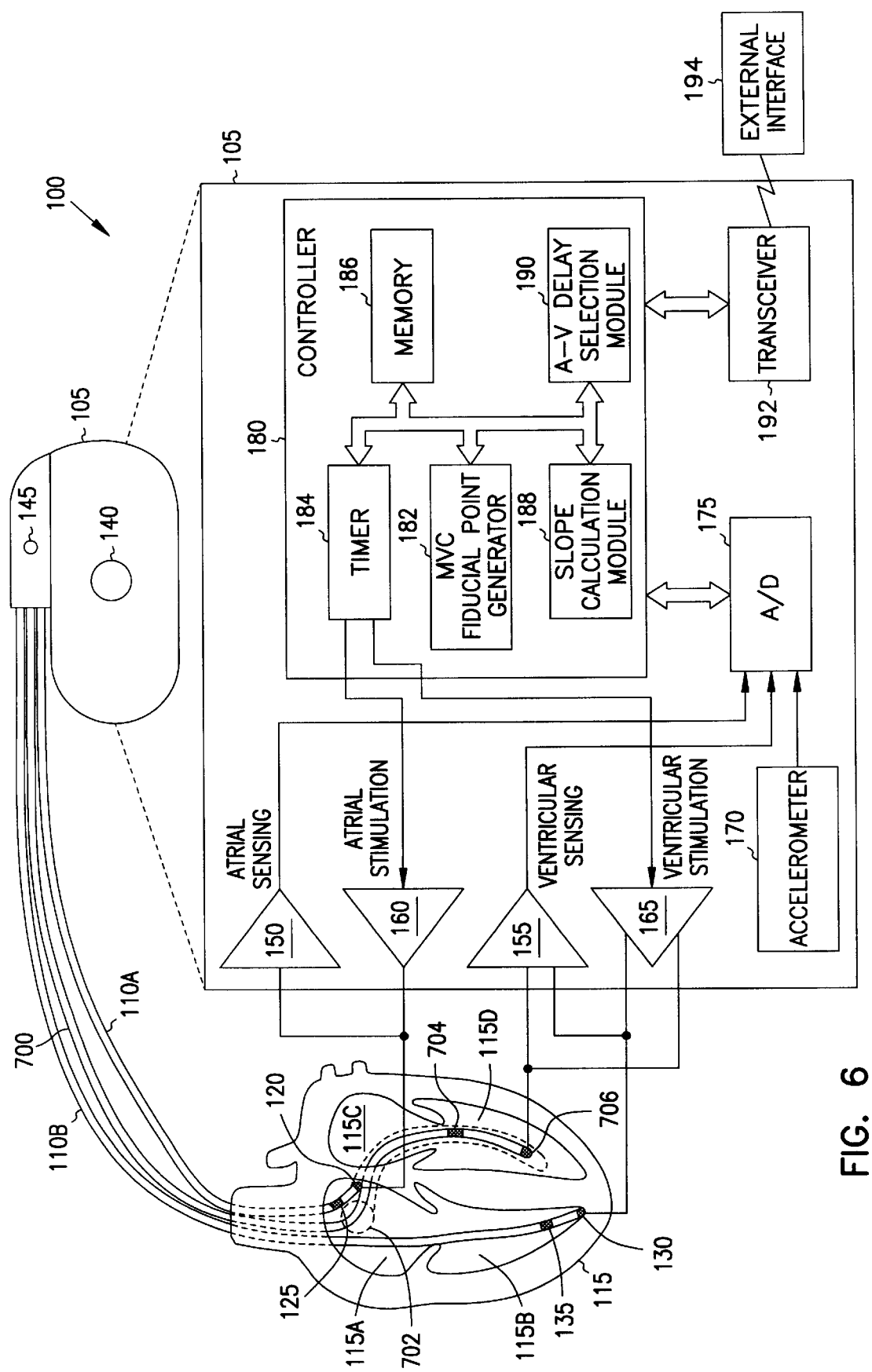
FIG. 6 is a schematic/block diagram illustrating generally, among other things, one embodiment of portions of a cardiac rhythm management system including an electrode associated with the left side of the heart, and an environment in which it is used.

Although the system and its operation have been particularly described above with respect to selecting an A-V delay for the delivery of right ventricular stimulations (for patients who respond to such therapy), it is understood that the system and its operation is even more applicable to selecting an A-V delay for the delivery of left ventricular stimulations or biventricular stimulations (for patients who respond to such therapy), as illustrated in the schematic/block diagram of FIG. 6. Moreover, the test values of A-V delay and/or the selected A-V delay value may be measured from either right or left atrial depolarizations (paced or sensed). In fact, the data illustrated in FIGS. 3 and 4 is illustrative of data actually obtained using A-V delays taken with respect to the left ventricle.

In FIG. 6, system 100 further includes a lead 700 having at least one electrode associated with left ventricle 115D, intravascularly, epicardially, or otherwise. In this example, lead 700 is introduced into association with left ventricle 115D by inserting lead 700 through right atrium 115A and into coronary sinus 702 and/or one of its tributaries such as the great cardiac vein. In this manner, an electrode, such as an approximately basal electrode 704 or a more apical electrode 706 is placed in association with a portion of left ventricle 115D for sensing or pacing left ventricular heart contractions. This arrangement also allows delivery of simultaneous or offset biventricular stimulations for coordinating the relative timing contractions of right and left ventricular heart contractions. It further allows the delivery of simultaneous or offset left ventricular stimulations for resynchronizing the spatial nature of the left ventricular depolarization by providing simultaneous or offset stimulations at more than one left ventricular electrode, such as at each of electrodes 704 and 706. The configuration illustrated in FIG. 6 may be used in conjunction with the above-discussed techniques for selecting the appropriate AV-delay, thereby establishing the AV delay value as measured from an atrium to one of electrodes 704 and 706. Such a configuration is particularly useful for, among other things, patients having left bundle branch block (LBBB).

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A system, including:
    an atrial module selected from the group consisting essentially of an atrial stimulation module and an atrial sensing module, the atrial module providing times associated with atrial depolarizations;
    a ventricular stimulation module;
    a mitral valve closure detector providing times associated with mitral valve closures; and
    an atrioventricular (A-V) timing module, coupled to the atrial module and the ventricular stimulation module, for controlling the delivery of ventricular stimulations at different A-V delays, the A-V timing module including:
        a timer, coupled to the mitral valve closure detector for receiving the times associated with mitral valve closures corresponding to the ventricular stimulations at the different A-V delays, and coupled to the atrial module for receiving the times associated with the atrial depolarizations, the timer calculating, for each of the ventricular stimulations at the different A-V delays, a time interval between the preceding atrial depolarization and a next mitral valve closure following that ventricular stimulation;
    a slope calculation module, coupled to the timer and calculating the slopes of the time intervals against the different A-V delays; and
    an A-V delay selection module, coupled to the timer and selecting one of the different A-V delays based on the time intervals obtained corresponding to the ventricular stimulations at the different A-V delays, and in which the A-V delay selection module is coupled to the slope calculation module to select an A-V delay based on the slopes of the time intervals.

2. The system of claim 1, further including:
    an atrial electrode configured for being associated with an atrium, and coupled to the atrial module; and
    a ventricular electrode configured for being associated with a ventricle, and coupled to the ventricular stimulation module.

3. The system of claim 1, in which the mitral valve closure detector includes an accelerometer, providing a heart acceleration signal including information about the mitral valve closures.

4. The system of claim 3, in which the mitral valve closure detector further includes a highpass filter, coupled to the accelerometer for receiving the heart acceleration signal and providing a highpass filtered heart acceleration signal.

5. The system of claim 4, in which the highpass filter is selected from the group consisting essentially of:
    a baseline removal highpass filter for removing a baseline component of the acceleration signal; and
    a differentiator, coupled to the accelerometer for receiving the heart acceleration signal and providing a first derivative heart acceleration signal.

6. The system of claim 5, in which the highpass filter is a differentiator and the mitral valve closure detector further includes a lowpass filter, coupling the accelerometer to the differentiator.

7. The system of claim 6, in which the mitral valve closure detector further includes a peak detector, coupled to the differentiator for receiving and detecting negative peaks of first derivative heart acceleration signal, and providing fiducial points representing mitral valve closures.

8. The system of claim 1, in which the timer includes memory including stored values of the different A-V delays and stored values of the time intervals corresponding to each of the different A-V delays, and in which the slope calculation module includes memory including stored values of the slopes of the time intervals corresponding to adjacent A-V delays.

9. The system of claim 8, in which the A-V delay selection module is included in a controller having a memory that includes a sequence of operations, the controller executing the sequence of operations for selecting the shortest of the A-V delays with which an adjacent shorter one of the A-V delays provides a larger slope than an adjacent longer one of the A-V delays.

10. The system of claim 8, in which the A-V delay selection module is included in a controller having a memory that includes a sequence of operations, the controller executing the sequence of operations for selecting a knee between the time intervals at small A-V delays and the time intervals at large A-V delays.

11. A system, including:
- an atrial electrode, configured to be associated with an atrium of a heart;
- an atrial module, selected from the group consisting of an atrial stimulation module and an atrial sensing module, the atrial module coupled to the atrial electrode, the atrial module providing times associated with atrial depolarizations;
- a ventricular electrode, configured to be associated with a ventricle of the heart;
- a ventricular stimulation circuit, coupled to the ventricular electrode for delivering ventricular stimulations;
- an accelerometer, configured to be associated with the heart for detecting and providing a heart acceleration signal;
- an accelerometer interface module, including an input coupled to the accelerometer for receiving the heart acceleration signal, and including an output providing fiducial point times associated with mitral valve closures obtained from the heart acceleration signal; and
- an atrioventricular (A-V) timing module, coupling the ventricular stimulation circuit to the ventricular electrode for delivering ventricular stimulations separated from corresponding preceding atrial depolarizations by different A-V delays, the A-V timing module including:
  - a timer, coupled to the accelerometer interface module for receiving the fiducial point times, and coupled to the A-V timing module for receiving the times associated with the atrial depolarizations, the timer calculating, for each ventricular stimulation associated with the different A-V delays, a P-MVC time interval between the atrial depolarization time and the fiducial point time following that ventricular stimulation;
  - a slope calculation module, calculating the slopes of the P-MVC time intervals against the different A-V delays; and
  - an A-V delay selection module, selecting one of the different A-V delays based on the slopes of the P-MVC time intervals.

12. A system, including:
- an atrial module, selected from the group consisting of an atrial stimulation module and an atrial sensing module, the atrial module configured to be coupled to an atrial electrode, the atrial module providing times associated with atrial depolarizations;
- a ventricular stimulation circuit, configured to be coupled to the ventricular electrode for delivering ventricular stimulations;
- an accelerometer, configured to be associated with the heart for detecting and providing a heart acceleration signal;
- an accelerometer interface module, including an input coupled to the accelerometer for receiving the heart acceleration signal, and including an output providing fiducial point times associated with mitral valve closures obtained from the heart acceleration signal; and
- an atrioventricular (A-V) timing module, coupled to the ventricular stimulation circuit to control delivery of ventricular stimulations separated from corresponding preceding atrial depolarizations by different A-V delays, the A-V timing module including:
  - a timer, coupled to the accelerometer interface module for receiving the fiducial point times, and coupled to the A-V timing module for receiving the times associated with the atrial depolarizations, the timer calculating, for each ventricular stimulation associated with the different A-V delays, a P-MVC time interval between the atrial depolarization time and the fiducial point time following that ventricular stimulation;
  - a slope calculation module, calculating the slopes of the P-MVC time intervals against the different A-V delays; and
  - an A-V delay selection module, selecting one of the different A-V delays based on the slopes of the P-MVC time intervals.

* * * * *